United States Patent [19]

Jacobsen et al.

[11] Patent Number: 4,613,331

[45] Date of Patent: Sep. 23, 1986

[54] ARTICULATED PROSTHETIC WRIST

[75] Inventors: Stephen C. Jacobsen, Salt Lake City; Harlan R. Wright, deceased, late of Salt Lake City, both of Utah; by Gail J. Pendell, general personal representative, La Mesa, Calif.

[73] Assignee: University of Utah, Salt Lake City, Utah

[21] Appl. No.: 658,192

[22] Filed: Oct. 5, 1984

[51] Int. Cl.$^4$ .................................................. A61F 2/58
[52] U.S. Cl. ........................................ 623/61; 623/62; 403/90; 403/129; 403/131
[58] Field of Search ..................... 3/12.4, 12.5, 12.6; 901/28, 29, 18; 403/90, 129, 131, 146; 623/65, 61, 62, 24, 25

[56] References Cited

U.S. PATENT DOCUMENTS 2,422,302 6/1947 Horn ...................................... 3/12.4
2,727,768 6/1952 Latzen ................................. 403/129
3,841,769 10/1974 Bowerman .......................... 403/90

Primary Examiner—Ronald L. Frinks
Assistant Examiner—James Prizant
Attorney, Agent, or Firm—Workman, Nydegger & Jensen

[57] ABSTRACT

The present invention provides an articulated artificial wrist capable of simple repositioning of an artificial hand attached thereto. A presently preferred embodiment of the present invention comprises a contractible spherical ball assembly that is normally expanded so as to tightly fit within a socket assembly. An actuating lever is provided such that, upon actuation, the lever causes contraction of the ball assembly, which allows for repositioning of the artificial hand. Release of the actuating lever secures the artificial hand in its new orientation by permitting the ball assembly to reexpand within the socket assembly. A second embodiment further provides for motorized rotation of the artificial hand independent of use of the actuating lever.

32 Claims, 5 Drawing Figures

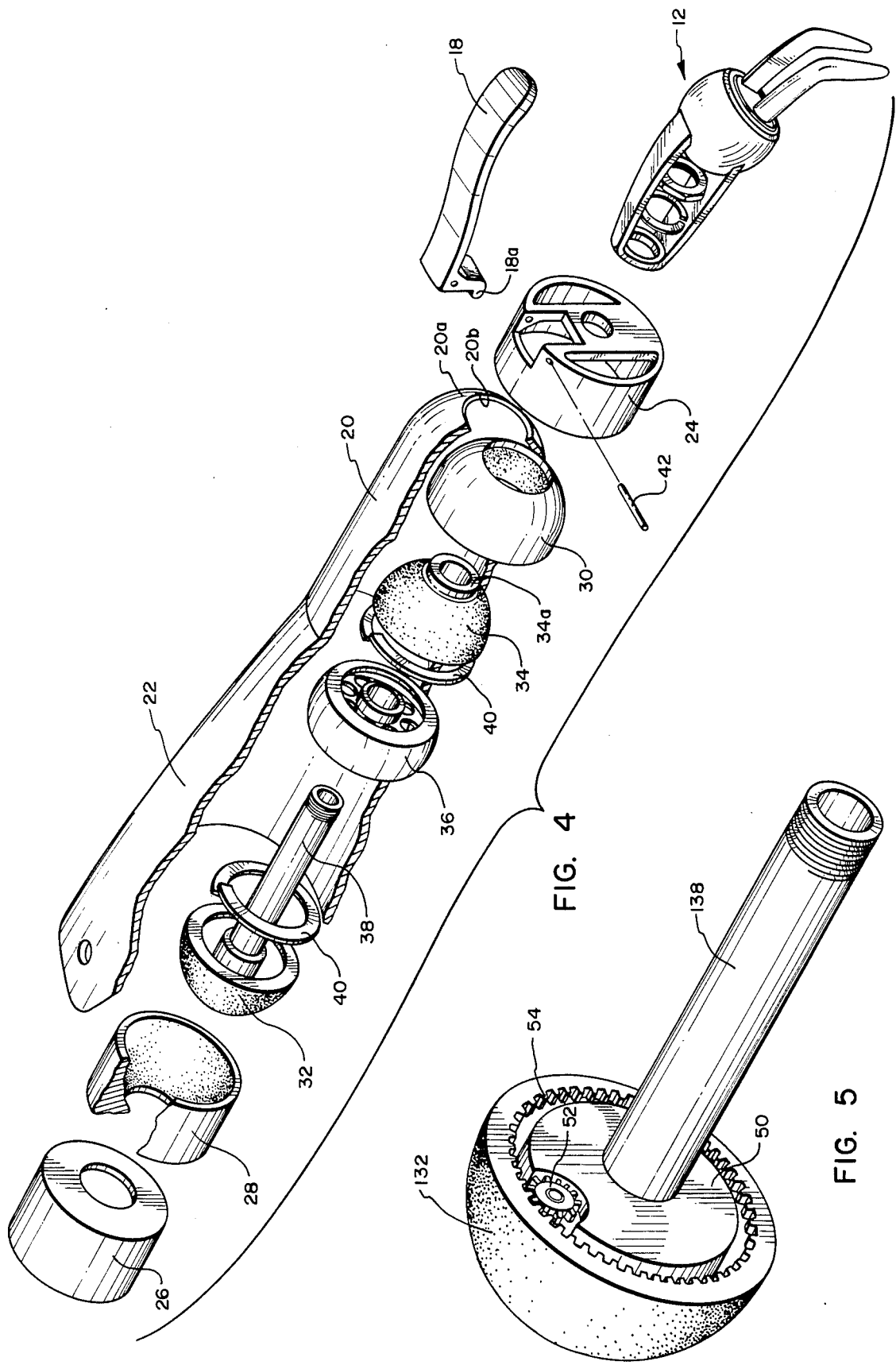

ARTICULATED PROSTHETIC WRIST

BACKGROUND

1. Field of the Invention

The present invention relates to the field of prosthetic appliances; more particularly, the present intention is directed to an articulated prosthetic wrist utilized as a component of a prosthetic arm.

2. The Prior Art

The technology of prosthetic arms has progressed tremendously from the era when a carved wooden arm having a hook on the end was strapped to the stump of a patient's damaged arm. In contrast, the present use of various microcircuits and small motors placed within lightweight prosthetic arms and controlled by electrodes affixed in contact with various large muscle groups, has resulted in articulated prosthetic arms capable of performing a multitude of tasks, thereby simulating to a significant extent the movements and functions of a natural arm.

Despite these overall advances in prosthetic arm technology, some components of prosthetic arms have undergone relatively little development. For example, the technology associated with prosthetic wrists remains quite rudimentary. Often, no attempt has even been made to provide any movement in the wrist region of the prothesis, and a hand is simply affixed directly to the end of the forearm of the prothesis.

Traditionally, when some type of prosthetic wrist has been used, it has typically only provided movement in one direction, such as side-to-side movement or up-and-down movement. A set pin or other securing mechanism has been used to achieve this degree of movement. Even though such one-directional movement is extremely limited, it does significantly increase the uses of the prosthetic hand and arm. Nevertheless, it will be appreciated that this type of one-directional movement is very limiting to the user and it does not provide the type of mobility and range of movement which is necessary for many functions.

In order to obtain a prosthetic wrist having some range of movement, the general approach has been to provide the hand with a small ball that is received by a corresponding socket secured to the forearm. A screw-fitting is placed around the ball and engaged with threads on the forearm to secure the ball within the socket under pressure sufficient to insure a friction fit. When the screw-fitting is tightly engaged with the threads on the forearm, the hand can be secured in the desired orientation.

Although this arrangement has been found capable of allowing orientation of the artificial hand to a variety of positions, its use has not been without disadvantages. For instance, in order to move the hand from one orientation to another, it is necessary to loosen the screw-fitting, reposition the hand, and then retighten the screw-fitting. Although this would be a simple task for a person with two hands, in practice it has been found somewhat troublesome to a person with only one natural hand.

For example, it has been found necessary to tighten the screw-fitting extremely tight in order to secure the hand in a desired position sufficiently that the hand does not move when it is used to perform a task. The torque necessary to tighten and loosen the screw-fitting has a tendency to unseat the prosthetic arm from its normal position on the patient's body, as well as being a difficult maneuver.

Additionally, after the screw-fitting has been loosened, the prosthetic hand tends to flop to a downward position due to the effects of gravity. Since the patient has only one useable hand to adjust the orientation of the prosthetic hand, it will be appreciated that it is extremely awkward to maintain the hand in a desired orientation while simultaneously tightening the screw-fitting.

The result of these problems has often been an unwillingness on the part of patients to reposition the prosthetic hand when moving from task to task, thereby rendering the need for an articulatable prosthetic wrist essentially superfluous.

Recently, researchers have attempted to utilize small motors in order to provide movement to simulate the functions of a natural wrist. Unfortunately, the use of motors in the small wrist region of the prothesis creates significant problems. For example, a larger than normal wrist has had to be historically used in order to house the motor and the associated gear mechanisms. Moreover, a significant problem is the substantial weight which is added when motors and the associated hardward are used in the prosthetic wrist. Weight is of critical importance when designing movable prosthetic arms, and the amount of weight added becomes especially important when it is placed near the distal end of the arm, such as at the wrist. The serious detrimental effects of adding additional weight has caused most developers of arms to reject the use of any type of a motorized prosthetic wrist.

In view of the foregoing, it will be appreciated that it would be a significant advancement in the field of prosthetic arms if a prosthetic wrist were to be provided that would permit simple and easy positioning of a prosthetic hand to a full range of the degrees of motion and yet would not add significant weight to the prosthetic arm. Such an improved articulated prosthetic wrist is disclosed and claimed herein.

BRIEF SUMMARY AND OBJECTS OF THE INVENTION

The present invention is directed to novel methods and apparatus for use in providing prosthetic wrists to be used as components of prosthetic arms. A preferred embodiment of the present invention comprises a contractible spherical ball assembly that is normally expanded to fill a corresponding spherical socket located at the distal end of an artificial forearm.

An actuating lever extending distally from the artificial wrist is provided such that upon actuation the lever will cause sufficient contraction of the spherical ball assembly to permit simple reorientation of a prosthetic hand attached to the ball assembly. Release of the actuating lever permits the ball assembly to expand once more within the spherical socket, thereby securing the hand in the selected orientation.

A second embodiment within the scope of the present invention further provides a motor for controlling rotation of a prosthetic hand independently of the actuating lever.

It is, therefore, a primary object of the present invention to provide improved methods and apparatus related to prosthetic wrists capable of movement in several degrees of motion so that the wrist can be stationarily oriented in essentially any position that a natural hand can be oriented.

It is another object of the present invention to provide methods and apparatus related to prosthetic wrists capable of being easily manipulated (such as with one hand) in order to position a prosthetic hand attached to a prosthetic arm into a desired orientation.

It is still another object of the present invention to provide a lightweight prosthetic wrist capable of easily controlled articulated movement.

It is a further object of the present invention to provide a prosthetic wrist which is capable of sustained rotational movement in a variety of positions.

These and other objects and features of the present invention will become more fully apparent from the following description and appended claims taken in conjunction with the accompanying drawings.

BRIEF DESCRIPTION OF THE DRAWINGS

In the accompanying drawings, which represent the best mode presently contemplated for carrying out the invention:

FIG. 4 is an exploded view of the embodiment of the present invention illustrated in FIGS. 1–3.

FIG. 5 is a perspective view of one of the components of the artificial wrist, drawn to a much larger scale, and illustrating one manner of incorporating an electric motor for use in rotation of an artificial hand.

DETAILED DESCRIPTION OF THE PREFERRED EMBODIMENTS

Figure 1:
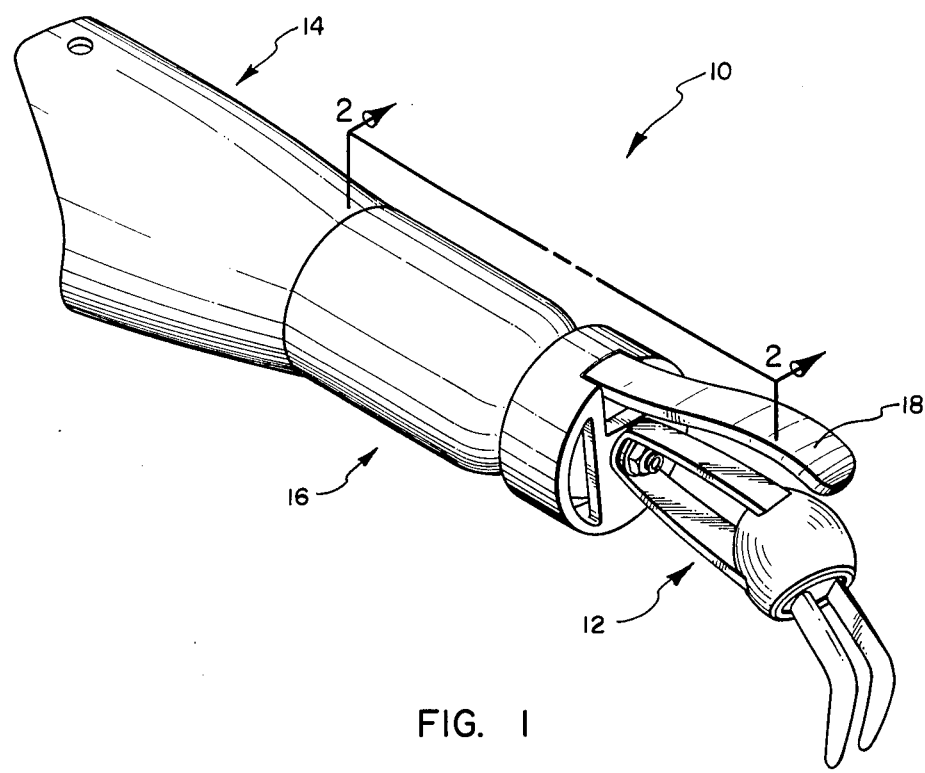
FIG. 1 is a perspective view of a portion of an artificial arm having attached thereto a preferred embodiment of a prosthetic wrist within the scope of the present invention.

The present invention can best be understood by reference to the drawings wherein like parts are designated with like numerals throughout. FIG. 1 illustrates a typical prosthetic arm 10 including an artificial hand 12 and an artificial forearm 14 secured together by means of an articulated artificial wrist 16. An actuator lever 18 is provided for use in repositioning artificial hand 12 from one orientation to another, as is more fully discussed hereinbelow.

Referring now to FIG. 4, which more clearly illustrates the various components comprising a presently preferred embodiment of the apparatus of the invention, it will be appreciated that wrist casing 20 may advantageously be fabricated contiguous with, and as a natural extension of, forearm casing 22. Preferably, forearm casing 22 and wrist casing 20 are constructed of a strong, yet lightweight material, such as epoxy-bond carbon filament-wound fiber, carbon-graphite fiber, or injection-molded nylon. For aesthetic purposes, it is also desirable to fabricate the forearm and wrist casings in a flesh tone corresponding to the flesh color of the patient to whom the prosthetic arm is to be fitted.

Wrist casing 20 may be of any suitable shape and dimension, but is preferably cylindrical in shape. Distal end 20a of the wrist casing is advantageously rounded so as to avoid interference with motion of actuator mount 24 when the mount is moved during repositioning of artificial hand 12. Rounded end 20a of the wrist casing can also be used as the bearing surface for actuator mount 24 so that no unsightly gaps occur during movement of the artificial hand.

Figure 2:
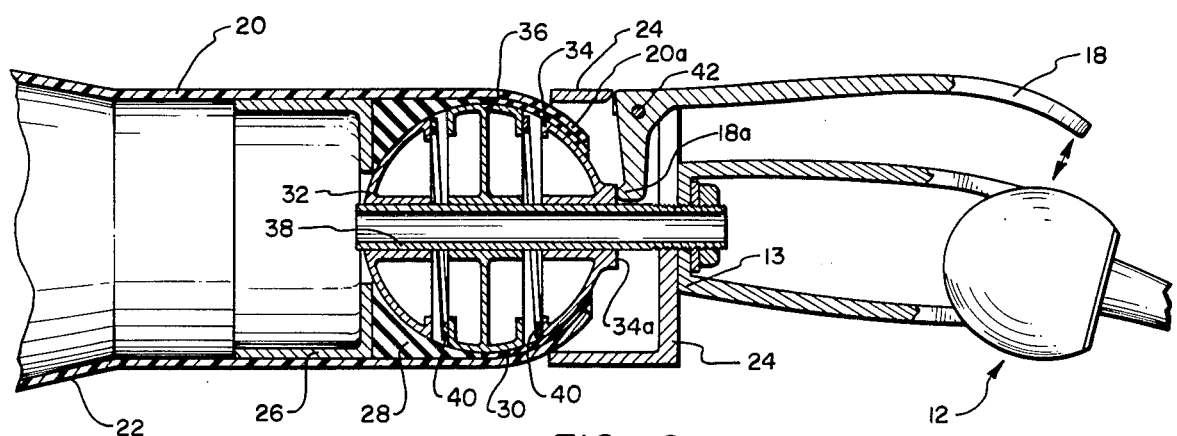
FIG. 2 is a longitudinal cross-sectional view of a portion of the prosthetic wrist of FIG. 1 taken along line 2—2 of FIG. 1 and drawn to a larger scale, illustrating the internal components comprising a presently preferred embodiment of an apparatus within the scope of the present invention.
Figure 3:
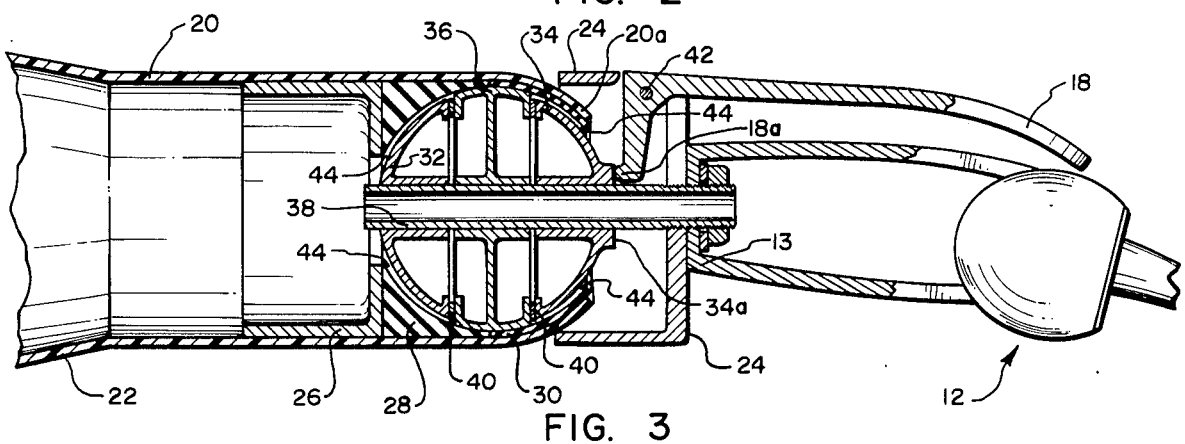
FIG. 3 is a longitudinal cross-sectional view similar to that of FIG. 2, except that retraction of the actuating lever prior to reposition of the orientation of the artificial hand is illustrated.

The articulated components of the illustrated embodiment include a pair of socket members 28 and 30 having hemispherical cavities formed therein. As best seen in FIGS. 2 and 3, socket member 30 fits snugly against the interior walls of rounded end 20a of the wrist casing, while socket member 28 is situated within wrist casing 20 so as to abut with socket member 30, thereby forming a spherical socket cavity within the two socket members. Retainer collar 26, which is adapted for securement within the proximal end of wrist casing 20, such as by threads (not shown), serves to retain the socket members within the proximal end of the wrist casing.

A ball assembly advantageously comprises a proximal semispherical member 32, a distal semispherical member 34, and an intermediate annular ring 36, and it is situated within the spherical cavity formed by socket members 28 and 30. A shaft 38 is advantageously secured to proximal semispherical member 32, and extends through a pair of spring washers 40, annular ring 36, distal semispherical member 34, socket member 30, and the open end 20b of wrist casing 20. Shaft 38 is then engaged with threads on actuator mount 24 and mounting plate 13 of artificial hand 12.

In certain embodiments, shaft 38 may advantageously be hollow so as to permit passage therethrough of electrical leads or actuating cables (not shown) connected to the artificial hand, thereby allowing for electrical control of the artificial hand. A hollow shaft also minimizes weight in the artificial wrist.

The dimensions of the various components of the ball assembly are such that the ball assembly fits snugly within the spherical cavity formed by socket members 28 and 30. When the ball assembly is positioned within the socket members, spring washers 40 are partially compressed so as to provide outward bias against semispherical members 32 and 34. Under these conditions, the semispherical members are biased outwardly against the hemispherical cavities of socket member 28 and 30, thereby resulting in a friction fit of the ball assembly within the socket assembly. If the outward bias caused by spring washers 40 is substantial enough, the ball assembly will tend to remain securely positioned at a predetermined orientation within the socket assembly, even when the artificial hand is utilized to perform various tasks.

Use of semispherical members 32 and 34 having relatively large surface areas and correspondingly large hemispherical cavities in socket members 28 and 30 results in substantial areas of contact between the socket assembly and ball assembly, thereby further enhancing the magnitude of the friction fit between these components. Additionally, roughening of the surface of semispherical members 32 and 34, and providing socket members 28 and 30 with slightly resilient interior surfaces is useful in further increasing the tendency of the ball assembly to remain positioned in a fixed, predetermined orientation within the spherical cavity formed by socket members 28 and 30.

Use of stronger spring washers 40 will also cause the ball assembly to fit more tightly within the socket assembly by increasing the outward bias of semispherical members 32 and 34 on the respective hemispherical cavities of socket members 28 and 30. Of course, the use of stronger spring washers also increases the force necessary to reposition the ball assembly from a selected orientation with the socket assembly during use of the artificial hand.

Appropriate selection of spring washers 40, the use of resilient material used in lining the surfaces of the hemispherical cavities in socket members 28 and 30, the modification of the texture of the surfaces of semispherical members 32 and 34, and other similar modifications, will alter the tendency of the ball assembly to remain fixedly positioned in a predetermined position within the socket assembly during routine tasks performed with artificial hand 12. The result of appropriate selection of these factors is that the artificial wrist has been found to have acceptable characteristics of stability for normal conditions.

It will be appreciated from the foregoing that spring washers 40 serve an important function in biasing semispherical members 32 and 34 outwardly against socket members 28 and 30 so as to secure the ball assembly in a desired orientation. As best seen in FIGS. 2 and 3, use of spring washers 40, or other suitable substitute therefor, further serves to make the ball assembly contractible. Causing contraction of the ball assembly will eliminate the tendency of the ball assembly to remain fixedly positioned in a particular predetermined orientation, thereby permitting repositioning of an artificial hand attached to the distal end of shaft 38. Since the ability to readily move the artificial hand is a highly desirable feature of any artificial wrist, the ability to easily cause contraction of the ball assembly is an important feature of the present invention.

In the embodiment illustrated in FIG. 2, actuator lever 18 is pivotally mounted to actuator mount 24 by means of a pin 42. The actuator lever is further provided with an offset foot 18a that rests against an annular extension 34a of distal semispherical member 34. Referring to FIG. 3, the act of depressing actuator lever 18 towards the artificial hand causes offset foot 18a to impinge against annular extension 34a, thereby compressing spring washers 40 and contracting the ball assembly. Contraction of the ball assembly causes the appearance of gaps 44 between the interior walls of socket members 28 and 30 and the corresponding semispherical members 32 and 34. When the ball assembly is so contracted, the ball assembly may then be easily repositioned.

Advantageously, annular ring 36 remains in contact with the interior walls of the socket members 28 and 30. This insures that the ball assembly will remain centered within the socket assembly even when contracted. Although it is to be understood that annular ring 36 could be omitted, such an omission would permit lateral movement of the ball assembly when contracted so that it is no longer centered within the socket assembly. This lateral movement would likely result in unwanted movement of the artificial hand as the semispherical members of the ball assembly become seated when the actuator lever is released. Additionally, it is generally more satisfying to a patient fitted with a prosthesis incorporating the artificial wrist of the present invention if the ball assembly maintains some contact with the walls of the socket members rather than flopping freely therein.

To insure smooth motion of the contracted ball assembly and to avoid damaging any resilient material secured to the hemispherical cavities of socket members 28 and 30, it is preferred that the outer surface of annular ring 36 be smooth and sized so as to be easily moved within the socket assembly.

Although the various components of an artificial wrist constructed in accordance with the present invention may be fabricated from any suitable material, it is highly preferable that a durable lightweight material be utilized in order to minimize the amount of weight added near the distal end of the prosthetic wrist. It is currently anticipated that a carbon graphite material having a thickness in the range of about 0.025–0.030 inches will be adequate for each of the various internal components. It is anticipated that metal be preferably avoided, except for use in constructing spring washers 40, in order to minimize the weight of the prosthesis.

A prosthetic wrist constructed according to the foregoing description is capable of unlimited movement and rotation within its range of motion. By merely grasping the base of the artificial hand and the actuator lever, it is a simple matter to depress the actuator lever so as to contract the ball assembly, reposition the artificial hand to desired angles of incidence and rotation, and release the actuator lever to secure the artificial hand in its new position. The present invention allows unprecedented ease of manual adjustment of the positioned orientation of an artificial hand.

Although it is very useful to provide an artificial wrist having manually operated six-degree mobility as described above (i.e., capable of articulated movement up and down, side to side, and rotation in either direction), it has been found that once an artificial hand is oriented to a desired angle of incidence for use in accomplishing a particular task, the angle of incidence is often left unchanged during the entire task.

On the other hand, for many uses, it is common to require frequent adjustments in the angle of rotation of the artificial hand. Yet, it is sometimes awkward to manually rotate the artificial hand above during the performance of a task since the patient's natural hand is likely engaged in a separate function. Accordingly, in many cases, it may be deemed desirable to provide means for motorized rotation of the artificial hand, despite the increase in weight that accompanies the addition of a motor.

FIG. 5 illustrates one manner in which a motor may be incorporated into a prosthetic wrist constructed in accordance with the present invention for purposes of rotation. In FIG. 5, it is seen that a motor 50 may be mounted within the interior of a semispherical member 132, which would otherwise corresponding to semispherical member 32 of the preferred embodiment of FIGS. 2–4. Shaft 138 is secured to motor 50, and the motor is itself rotatably secured within the interior of semispherical member 132.

Recognizing that semispherical member 132 will be in a substantially fixed position when a ball assembly incorporating that component is in an expanded condition, it will be appreciated that motorized rotation of drive gear 52 in cooperation with gear 54 (which is either secured to or formed integrally as a part of semispherical member 132) will cause rotation of shaft 138 and any artificial hand secured thereto. The motor may be operated so as to effect either clockwise or counterclockwise rotation of the artificial hand by any convenient control means. Of course, it would be preferable that the operator of the control means not necessarily require use of the patient's natural hand; this would permit the patient to perform tasks requiring simultaneous use of two hands.

It will be appreciated from the foregoing that the apparatus of the present invention provides for a convenient and easily usable articulated artificial wrist of lightweight construction. Unlike earlier prosthetic wrists that were awkward and inconvenient to use, an artificial hand attached to an artificial wrist constructed in accordance with the present invention can easily be adjusted in a matter of seconds to any position within its range of movement. Use of a ball and socket assembly having a large surface area assists in maintaining the ball assembly firmly in place once positioned, yet minimizes the amount of outward bias required between the ball assembly and socket assembly.

Although the apparatus of the present invention has been shown and described in reference to one particular embodiment, it is to be understood that the apparatus of the invention may also be embodied in other specific forms without parting from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Latters Patent is:

1. An articulated artificial wrist for use with a hand prosthesis, comprising:
    contractible ball means, said ball means comprising two semispherical ball members and bias means positioned between the semispherical ball members so as to bias the two semispherical ball members apart to a normally expanded configuration;
    connecting means having proximal and distal ends, said proximal end being secured to the ball means and said distal end being secured to the hand prosthesis;
    socket means for receiving the ball means, said socket means adapted to secure the ball means in a desired orientation when the ball means is in the normally expanded configuration;
    means for contracting the ball means such that, when contracted, said two semispherical ball members are both released from engagement with said socket means and the ball means is capable of being positioned within the socket means; and
    means for securing said socket means to a limb prosthesis for attachment to the remaining portion of an amputated limb.

2. An articulated artificial wrist as defined in claim 1 wherein the socket means is substantially spherical in shape.

3. An articulated artificial wrist as defined in claim 1 wherein the ball means is secured to the proximal end of an artificial hand and the socket means is secured to an artificial forearm.

4. An articulated artificial wrist as defined in claim 1 wherein the ball means further comprises an annular member positioned between the two semispherical ball members.

5. An articulated artificial wrist as defined in claim 4 wherein the bias means comprises two spring washers, with one spring washer being positioned between the annular member and the respective semispherical ball members.

6. An articulated artificial wrist as defined in claim 5 wherein said two semispherical ball members comprise proximal and distal semispherical ball members, and said connecting means comprises a shaft member having a proximal end secured to the proximal semispherical ball member, said shaft member passing through the spring washers, the annular member, and the distal semispherical ball member, and said shaft member being secured on its distal end to the hand prosthesis.

7. An articulated artificial wrist as defined in claim 1 wherein the ball means and the socket means have a substantial area of surface contact which fixedly secures the ball member within the socket member when the ball member is in its normally expanded configuration.

8. An articulated artificial wrist as defined in claim 1 wherein the ball means and the socket means have a substantial area of surface contact which fixedly secures the ball member within the socket member when the ball member is in its normally expanded configuration.

9. An articulated artificial wrist as defined in claim 4 wherein the ball means and socket means have a substantial area of surface contact therebetween so as to firmly secure the ball member within the socket member when the ball member is in its normally expanded configuration.

10. An articulated artificial wrist as defined in claim 1 wherein the socket means is provided with a resilient surface and wherein at least a portion of the surface of the ball means is provided with a texture suitable to assist in securing the ball means in a desired orientation.

11. An articulated artificial wrist as defined in claim 1 further comprising an actuator means and wherein the actuator means may be actuated simultaneously as the hand prosthesis is grasped for reorientation.

12. An articulated artificial wrist as defined in claim 6 further comprising an actuator assembly, said actuator assembly comprising:
    an actuator mount secured to said shaft member proximally adjacent to the artificial hand; and
    actuator means adapted to contract the ball assembly by applying pressure on the distal portion of the ball assembly when actuated.

13. An articulated artificial wrist as defined in claim 12 wherein said actuator means comprises a pivotally mounted actuator lever having a portion in contact with a distal portion of the distal semispherical ball member, said actuator means being adapted to displace the distal semispherical ball member proximally when actuated.

14. An articulated artificial wrist as defined in claim 1 further comprising means for effecting motorized rotation of the hand prosthesis without contracting said ball means.

15. An articulated artificial wrist as defined in claim 6 further comprising means for effecting motorized rotation of the hand prosthesis without contracting said ball means.

16. An articulated artificial wrist as defined in claim 15, wherein the means for effecting rotation of the hand prosthesis comprises a motor adapted to effect rotation of the shaft member without causing rotation of the ball assembly, such that rotation of the shaft causes rotation of the artificial hand secured thereto.

17. An articulated artificial wrist, comprising:
    ball means, said ball means including a distal semispherical ball member and a proximal semispherical ball member, and means for biasing the semispherical ball members apart to a normally expanded configuration;

socket means for receiving the ball means, said socket means being adapted to secure the ball means in a desired orientation when the ball means is in a partially expanded configuration;

shaft means having a proximal end secured to the proximal semispherical ball member, the shaft means being secured on its distal end to an artificial hand;

means for contracting the ball means such that, when contracted, both semispherical ball members are released from engagement with said socket means and the ball means is capable of being repositioned within the socket means; and support means for supporting the socket means on a forearm prosthesis adapted to be secured to the remaining portion of an amputated limb.

18. An articulated artificial wrist according to claim 17 wherein the ball means further comprises an annular member positioned between the semispherical ball members, said annular member having a diameter corresponding substantially to the diameter of the socket means.

19. An articulated artificial wrist according to claim 18, wherein the bias means comprises two spring washers, with one spring washer being positioned between the annular member and the respective semispherical ball members.

20. An articulated artificial wrist as defined in claim 19 wherein said shaft means comprises a shaft member having a proximal end secured to the proximal semispherical ball member, said shaft member passing through the spring washers, the annular member, and the distal semispherical ball member, and said shaft member being secured on its distal end to the artificial hand.

21. An articulated artificial wrist as defined in claim 17 wherein the ball means and the socket means have a substantial area of surface contact which fixedly secures the ball member within the socket member when the ball member is in its normally expanded configuration.

22. An articulated artificial wrist as defined in claim 17 wherein the socket means is provided with a resilient surface and wherein at least a portion of the surface of the ball means is provided with a texture suitable to assist in securing the ball means in a desired orientation.

23. An articulated artificial wrist as defined in claim 17 further comprising an actuator assembly, said actuator assembly comprising:

an actuator mount secured to said shaft means proximally adjacent to the artificial hand; and actuator means adapted to contract the ball assembly by applying pressure on the distal portion of the ball assembly when actuated.

24. An articulated artificial wrist as defined in claim 23 wherein said actuator assembly comprises a pivotally mounted actuator lever having a portion in contact with a distal portion of the distal semispherical ball member, said actuator means being adapted to displace the distal semispherical ball member proximally when actuated.

25. An articulated artificial wrist as defined in claim 17 further comprising means for effecting motorized rotation of the artificial hand without contracting said ball means.

26. A prosthetic arm having an articulated artificial wrist, comprising:

ball means secured to the proximal end of an artificial hand means, said ball means including a distal semispherical ball member and a proximal semispherical ball member, and means for biasing the semispherical ball members apart to a normally expanded configuration;

socket means for receiving the ball means, said socket means being secured to an artificial forearm, said artificial forearm adapted to be secured to the remaining portion of an amputated arm, said socket means being adapted to secure the ball means in a desired orientation when said ball means is in the normally expanded configuration; and means for contracting the ball means such that, when contracted, both said semispherical ball members are released from engagement with the socket means and said ball means is capable of being repositioned within the socket means.

27. A method for positioning an artificial hand at a desired orientation with respect to an artificial forearm, comprising the steps of:

providing a prosthetic arm including artificial hand means secured to contractible ball means and socket means adapted to receive the ball means secured to artificial forearm means, said ball means being biased to a normally expanded configuration within the socket means so as to be secured in a desired orientation with the socket means;

contracting the ball means so that the ball means is released from engagement with the socket means and is capable of being repositioned within the socket means together with repositioning of the artificial hand means attached thereto;

positioning the artificial hand means to a desired orientation; and causing the ball means to re-expand within the socket means so as to secure the ball means at its new orientation within the socket means.

28. A method for positioning an artificial hand as defined in claim 27 wherein the artificial wrist further includes an actuator member capable of contracting the ball means upon actuation thereof, and wherein the step of contracting the ball means is accomplished by actuating the actuator member.

29. A method for positioning an artificial hand as defined in claim 27, wherein the ball means comprises a distal semispherical ball member and a proximal semispherical ball member and bias means biasing said semispherical ball members apart, and a shaft member having a proximal end secured to the proximal semispherical ball member and extending through the bias means and distal semispherical ball member, and being secured on its distal end to the artificial hand.

30. A method for positioning an artificial hand as defined in claim 29 wherein the ball assembly further comprises an actuator assembly, said actuator assembly including an actuator mount secured to the shaft member proximally adjacent to the artificial hand, and actuator means adapted to contract the ball assembly by applying pressure on the distal portion of the ball assembly when actuated, and wherein the step of contracting the ball means is accomplished by actuating the actuator means.

31. A method for positioning an artificial hand as defined in claim 30 wherein the artificial hand is manually positioned to a new orientation by grasping the artificial hand, and wherein the actuator means is adapted to be actuated simultaneously with grasping the artificial hand so that the artificial hand may be easily repositioned.

32. A method for positioning an artificial hand as defined in claim 27 wherein the ball means is further provided with motorized means for rotating the artificial hand, and further comprising the step of rotating the artificial hand to a suitable angle.

* * * * *

UNITED STATES PATENT AND TRADEMARK OFFICE
CERTIFICATE OF CORRECTION

PATENT NO. : 4,613,331

DATED : September 23, 1986

INVENTOR(S) : Stephen C. Jacobsen and Harlan R. Wright

It is certified that error appears in the above-identified patent and that said Letters Patent is hereby corrected as shown below:

Col. 1, line 7, "intention" should be --invention--

Col. 6, line 51, "corresponding" should be --correspond--

Col. 7, line 29, "Latters" should be --Letters--

Signed and Sealed this

Twenty-third Day of December, 1986

Attest:

DONALD J. QUIGG

Attesting Officer     Commissioner of Patents and Trademarks